United States Patent [19]

Yang et al.

[11] Patent Number: 4,757,064

[45] Date of Patent: Jul. 12, 1988

[54] PHARMACOLOGICALLY ACTIVE BICYCLIC LACTAMS

[75] Inventors: Ming-he Yang; Yan-rong Chen; Geng-tao Liu; Liang Huang, all of Beijing, China

[73] Assignees: Bayer Aktiengesellschaft, Leverkusen, Fed. Rep. of Germany; Chinese Academy of Medical Sciences, Beijing, China

[21] Appl. No.: 4,985

[22] Filed: Jan. 20, 1987

[30] Foreign Application Priority Data

Jan. 20, 1986 [GB] United Kingdom ............... 8601256

[51] Int. Cl.$^4$ .................. A61K 31/395; C07D 225/06
[52] U.S. Cl. ..................................... 314/183; 540/461
[58] Field of Search ......................... 540/461; 514/183

[56] References Cited

PUBLICATIONS

Hackh's Chemical Dictionary, 4th Ed., (1922), (McGraw-Hill), p. 16 & cover page & copyright page. Chemical Abstracts, vol. 73, (1970), abstracting Pecherer et al, Helv. Chim. Acta (1970), vol. 53, No. 4, pp. 763–770 (German).

Primary Examiner—Robert T. Bond
Attorney, Agent, or Firm—Sprung Horn Kramer & Woods

[57] ABSTRACT

A pharmacologically active phenyl-substituted bicyclic lactam has been isolated from the leaves of *Clausena lansium*. This compound and its derivatives have the formula

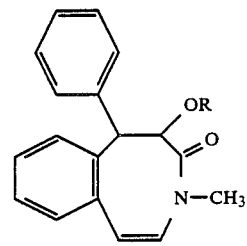

Where R is hydrogen of a $C_1$–$C_{18}$-acyl group. It has been found that these compounds are useful in the treatment of hypoxia and as antiamnestics.

6 Claims, No Drawings

PHARMACOLOGICALLY ACTIVE BICYCLIC LACTAMS

The present invention relates to a new pharmacologically active phenyl-substituted bicyclic lactam its isolation from plants of the Rutaceae Clausena species, derivatives of said bicyclic lactam and its use as pharmaceutically active agent. The invention is also concerned with pharmaceutical compositions containing said bicyclic lactam or its derivatives and with their manufacture.

Rutaceae *Clausena anicata* was reported to be used as a folk medicine in certain parts of Africa (I. Mester et al., Planta Medica 32 (1) 81, 1977). It has also been reported that the crude extract of *Clausena indica* Oliv. has cardiovascular activity and that two coumarin derivatives, Clausmarins A and B, isolated (TLC) from *Clausena Pentaphylla* (Roxb.) showed spasmolytic activity in animal tests (Dhan Prakash et al., Phytochem. 17, 1194, 1978; Aboo Shoeb et al., J.C.S. Chem. Commun. 281, 1978). About fifty constituents have already been isolated from the roots, stems, etc. of various species of Clausena. Most of these constituents are derivatives of coumarin, carbazole and terpene; so far only two linear carboxylic acid amides were reported to be present in the leaves of Clausena plants (S. R. Johns et al., Aust. J. Chem. 20, 2795, 1967; Dhan Prakash et al., Indian J. Chem. Sect. B 19B (12), 1075, 1980)

It has now been found that the leaves of *Clausena lansium* contain a bicyclic lactam which contains a phenyl substituent.

This compound and its derivatives were found to have various valuable pharmacological properties. The structures of these compounds have been confirmed by chemical derivatisation and by spectral data.

The present invention is directed to compounds of the general formula:

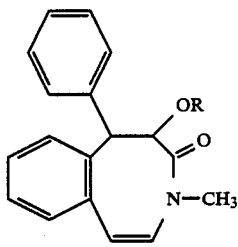

(I)

wherein R represents hydrogen or an acyl group having 1 to 18 carbon atoms.

Preferred compounds according to general formula (I) are those wherein
R represents hydrogen or an acyl group having 1 to 4 carbon atoms.

Especially preferred are those compounds wherein R represents hydrogen or the acetyl group.

The present invention is also directed to the isolation of the lactam of general formula (I, R=H) by a method which comprises the steps of:
(a) treating leaves of *Clausena lansium* with boiling water,
(b) adding dilute acid (e.g. HCl) to the concentrated aqueous extract,
(c) passing the supernatant through a column of cation ion exchange resin (preferably in its H+-form),
(d) treating the resin with a base, preferably aqueous ammonia,
(e) extracting the resin with an organic solvent such as ethers, chloroform, methylene chloride, acetic acid esters of $C_1-C_6$ alcohols or $C_2-C_6$ ketones, preferably with diethyl ether,
(f) chromatographing the concentrated extract on silica or aluminum oxide column with chloroform, methylene chloride, ether or a chloroform/methanol mixture as eluting agent and
(g) collecting and concentrating the eluate with an Rf-value of 0.64 on TLC (silica gel plate, $CHCl_3:MeOH=97:3$ as eluting agent).

It is preferred to recrystallize the crude product obtained by the above isolation methods from alcohols, e.g. methanol or ethanol.

Acyl derivatives of the compound may be synthesized by acylation methods known per se.

The present invention also relates to pharmaceutical compositions and medicaments containing compounds of formula (I) as an active ingredient and to the manufacture of these compositions.

The invention is also directed to the use of compounds of formula (I) for the treatment of hypoxia and amnesia, as hepatoprotective agents against chemical toxins and for increasing the detoxificating function of the liver.

The compounds of the formula (I) in animal experiments have a pronounced cerebral hypoxia protective and anti-amnestic effect which is significantly stronger than that of piracetam which is the structurally most closely related compound in the area of cerebral therapeutics and nootropics.

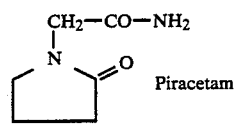

Piracetam

Even at high doses the animals do not show any significant changes in their behaviour. The hypoxia protective effect apparently is not caused by an unspecific sedation, therefore, which would give rise to a reduced need for oxygen. The acute toxicity of the compounds of the formula (I) was found to be very low.

When tested for hepatoprotective action the compounds of formula (I) decreased the elevated serum transaminase (SGPT) of mice intoxicated with $CCl_4$.

The pharmaceutical compositions according to the invention may for example take the form of ointments, gels, pastes, creams, sprays (including aerosols), lotions, suspensions, solutions and emulsions of the active ingredient in aqueous or non-aqueous diluents, syrups, granules or powders.

The compositions are preferably in the form of a sterile isotonic aqueous solution or in the form of tablets, capsules, pills and suppositories comprising a compound according to the invention either alone or in admixture with a diluent.

The diluents to be used in pharmaceutical compositions (e.g. granulates) adapted to be formed into tablets, dragees, capsules and pills include the following:
(a) fillers, e.g. starch, sugars and silicic acid;
(b) binding agents, e.g. cellulose derivatives, alginates, gelatine and polyvinyl pyrrolidone;
(c) moisturizing agents, e.g. glycerol;

(d) disintegrating agents, e.g. agar-agar, calcium carbonate and sodium bicarbonate;
(e) resorption accelerators, e.g. quarternary ammonium compounds;
(f) surface active agents, e.g. cetyl alcohol;
(g) adsorptive carriers, e.g. kaolin and bentonite;
(h) lubricants, e.g. talc, calcium and magnesium stearate and solid polyethylene glycols, The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in micro-encapsulated form together with one or several of the above-mentioned diluents.

The production of the above-mentioned pharmaceutical compositions and medicaments is carried out by any method known in the art, for example by mixing the active ingredient(s) with the diluent(s) to form a pharmaceutical composition (e.g. a granulate) and then forming the composition into the medicament (e.g. tablets).

The pharmaceutical compositions according to the invention preferably contain about 0.1 to 99.5, more preferably from about 0.5 to 95% of the active ingredient by weight of the total composition.

The preferred daily dose for administration of the medicaments of the invention is 0.001 mg to 0.2 mg of the active ingredient.

The following Examples illustrate the invention.

EXAMPLE 1

Isolation of the compound of the formula

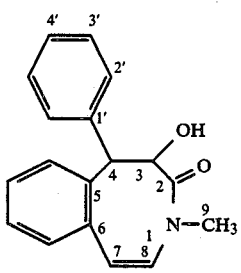

80 kg of dried leaves of *Clausena lansium* (Lour) Skeels were boiled with water. The aqueous extract was concentrated to give 18 kg of crude syrup, 16 kg of crude syrup were treated with 0.06 N HCl (80 l) and the supernatant was passed through a column of wet $H^+$-form cation ion exchange resin (from 48 kg of $Na^+$-form cation ion exchange resin). The resin was then washed with deionized water, treated with 2% aqueous $NH_4OH$ (32.2 l) and finally extracted with diethyl ether (60 l). The concentrated ether extract as a syrup was chromatographed repeatedly on silica gel columns containing 20-100 times of its weight with chloroform as eluting agent. The concentrated chloroform eluate with $R_f$=0.64 on TLC was collected and concentrated. The crystals thus obtained were recrystallized from methanol. 2.22 g of white prism crystals, m.p. 187° to 188° C., were obtained.

$[\alpha]_D^{24.5}=0.00°$ (0.225 in $CHCl_3$).

Elementary analysis:

| | calculated (for $C_{18}H_{17}NO_2$) | found |
| --- | --- | --- |
| C % | 77.42 | 77.53 |
| H % | 6.09 | 6.12 |
| N % | 5.02 | 4.94 |

High resolution—MS $M^+$=279.1262.

$IR\gamma_{max}^{KBr}$ cm$^{-1}$: 3330 (OH), 1635 (amide-carbonyl), 3050, 3020, 1600, 1490, 760, 700 (benzene rings).

$UV\lambda_{max}^{MeOH}$ nm (log $\epsilon$): 208 (4.41), 247 (3.83).

$H^1$—NMR (in $CDCl_3$); chemical shift and assignment:

| δppm (J, Hz) | hydrogen |
| --- | --- |
| 2.92 (s; 3H) | N—CH$_3$ |
| 4.12 (d; J = 9; 1H) | C$_4$—H |
| 5.10 (d; J = 9; 1H) | C$_3$—H |
| 6.18 (d; J = 8; 1H) | C$_7$—H |
| 6.82 (d; J = 8, 1H) | C$_8$—H |
| 6.96-7.50 (m; 9H) | aromatic H |

$^{13}C$—NMR in $CDCl_3$; chemical shift and assignment:

| carbon | ppm |
| --- | --- |
| 2 | 172.3 |
| 3 | 72.4 |
| 4 | 57.8 |
| 9 | 32.6 |
| 1 | 131.6 |
| 6 | 144.9 |
| 5 | 140.0 |
| the rest nine aromatic carbons | 126.3 \| 129.9 |

The above compound was acetylated with acetic anhydride in pyridine to give a white crystalline solid, m.p. 187°-188°. The elementary analysis and spectrometric data indicated the product being the acetate.

Elementary analysis:

| | calculated (for $C_{20}H_{19}O_3N$) | found |
| --- | --- | --- |
| C % | 74.77 | 74.76 |
| H % | 5.92 | 5.94 |
| N % | 4.36 | 4.30 |

$IR\gamma_{max}^{film}$ cm$^{-1}$: 1730, 1720 (C=O), 1660(amide C=O), 1630(double bond), 1220(C-O).

Ms m/z(%): 321($M^+$, 20), 279(10), 250(8), 222(28), 192(100), 178(12), 165(11), 144(30), 91(13), 77(7), 43(51).

$^1H$—NMR (in $CDCl_3$); chemical shift and assignment:

| δppm (J, Hz) | hydrogen |
| --- | --- |
| 2.02 (s,3H) | CH$_3$COO— |
| 2.92 (s,3H) | CH$_3$N— |
| 4.57 (d, J = 10, 1H) | C$_4$—H |
| 6.08 (d, J = 10, 1H) | C$_3$—H |
| 6.41 (d, J = 8, 1H) | C$_7$—H |
| 6.86 (d, J = 8, 1H) | C$_8$—H |
| 7.10-7.32 (m, 9H) | aromatic H |

EXAMPLE 2

Influence of compounds according to the invention on liver functions.

Male Kunming strain mice weighing 18–22 grams were used throughout the experiments. The compounds to be tested were suspended in 5% Tween 80 and given orally by gavage. The vehicle of 5% Tween 80 solution was administered to control mice via the same route. In in vitro experiments, the compounds were dissolved in dimethylformamide and added directly into the incubation mixture.

Hepatoprotective action

Mice were divided into several groups. The control group was administered the vehicle. The other groups were given two doses (250 mg/kg) of compound (I, R=H), at an interval of 8 h, respectively. 10 ml/kg of 0.1% $CCl_4$ in vegetable oil was injected ip 24 h after the second administration of the compound. The mice were fasted for 16 h and sacrificed by decapitation. SGPT and liver lipids were determined. A piece of liver was processed into sections for pathological observation.

As shown in the following table 1 compound (I, R=H) significantly decreased the elevated SGPT of mice intoxicated with $CCl_4$.

TABLE 1

Effect of compound (I, R = H) (250 mg/kg × 2) isolated from the leaves of *Clausena lansium* (Lour) Skeels on SGPT levels of $CCl_4$ intoxicated mice (9 per group).

| Constituents | SGPT unit % $X \pm SE$ | P |
|---|---|---|
| Control | 2270 ± 284 | |
| Compound (I, R = H) | 617 ± 166 | <0.01 |

EXAMPLE 3

Influence of the compound (I, R=H) on retrograde amnesia (rat) under hypoxic conditions.

The apparatus (39 cm long, 21 cm high, and 21 cm wide) consists of two compartments, one made of translucent plastic (29 cm long) and the other one painted black (10 cm long). It has a bottom of spaced metal grids which are connected to a stimulating device delivering 1.6 mA for 20 s.

Both compartments are connected via a door which can be closed.

Male rats (100–120 g body weight) will be placed individually in the large compartment and allowed to explore both compartments for 3 min.

Thereafter, the animals are placed in the small (dark) compartment, the connecting door is closed and the foot shock is delivered. After that the animals are put in an air-tight cage which is perfused by a gas mixture containing 3.8% oxygen and 96.2% nitrogen. The animals are exposed to this hypoxic atmosphere until they exhibit gasping indicating ongoing respiratory failure (maximally 15 min).

24 hours later the rats are placed again in the bright compartment. The observation time is 3 min.

One experiment is performed in three groups of 15 animals each:

Group A: control group, not exposed to hypoxia
Group B: control group, receiving hypoxia after first training
Group C: treated animals, receiving hypoxia after first training
Evaluation: the times the animals need to enter the dark compartment are measured in seconds.

The time difference between the two control groups is considered to be 100% (A−B=100%).

The time difference between the control group B and the treated group C is calculated in percent (C−B=X%). X is considered to be a measure for the potency of the antiamnestic effect of the substrate tested.

TABLE 2

| Compound I, R = H (mg/kg p.o.) | X (%) |
|---|---|
| 100 | 34 |

We claim:
1. A compound of the formula

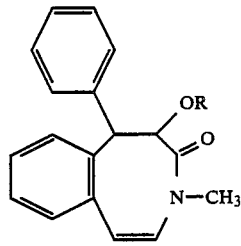

wherein R represents hydrogen or an acyl group having 1 to 4 carbon atoms.

2. A compound according to claim 1, wherein R represents hydrogen or an acetyl group.

3. A compound according to claim 1, wherein R represents hydrogen of the formula

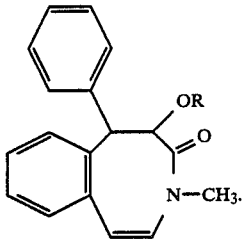

4. A method for the isolation of the compound according to claim 3 from the leaves of *Clausena lansium* which comprises the steps of:
   (a) treating leaves of *Clausena lansium* with boiling water,
   (b) adding dilute acid to the concentrated aqueous extract,
   (c) passing the supernatant through a column of cation ion exchange resin,
   (d) treating the resin with a base,
   (e) extracting the resin with an organic solvent,
   (f) chromatographing the concentrated extract on silica or aluminum oxide column with chloroform, methylene chloride, ether or chloroform/methanol mixture as eluting agent and
   (g) collecting and concentrating the eluate with an $R_f$-value of 0.64 on TLC (silica gel plate, $CHCl_3$:MeOH=97:3 as eluting agent).

5. A pharmaceutical composition useful in the treatment of hypoxia and amnesia or as a hepato-protective agent comprising an amount effective therefor of a compound according to claim 1 and a pharmaceutically acceptable diluent.

6. A method of treating acute or chronic viral hepatitis, liver intoxication, hypoxia or amnesia comprising administering to a patient in need of such treatment an effective amount of a compound according to claim 1.

* * * * *